United States Patent [19]
Goodman

[11] Patent Number: 5,827,180
[45] Date of Patent: Oct. 27, 1998

[54] METHOD AND APPARATUS FOR A PERSONAL HEALTH NETWORK

[75] Inventor: David F. Goodman, San Francisco, Calif.

[73] Assignee: LifeMasters Supported SelfCare, So. San Francisco

[21] Appl. No.: 978,892

[22] Filed: Nov. 26, 1997

Related U.S. Application Data

[63] Continuation of Ser. No. 518,783, Aug. 24, 1995, abandoned, which is a continuation-in-part of Ser. No. 334,936, Nov. 7, 1994, abandoned.

[51] Int. Cl.[6] ............................................. A61N 5/04
[52] U.S. Cl. .................................................. 600/300
[58] Field of Search ........................... 600/300, 301, 600/529; 128/920–925

[56] References Cited

U.S. PATENT DOCUMENTS

| | | |
|---|---|---|
| 3,968,900 | 7/1976 | Stambuk . |
| 3,991,908 | 11/1976 | Thomas et al. . |
| 4,018,358 | 4/1977 | Johnson et al. . |
| 4,034,757 | 7/1977 | Glover . |
| 4,047,635 | 9/1977 | Bennett, Jr. . |
| 4,054,343 | 10/1977 | Heyland . |
| 4,057,145 | 11/1977 | Wray et al. . |
| 4,155,003 | 5/1979 | Grassme . |
| 4,223,801 | 9/1980 | Carlson . |
| 4,254,871 | 3/1981 | Poore . |
| 4,261,468 | 4/1981 | Krebs . |
| 4,293,845 | 10/1981 | Villa-Real . |
| 4,295,664 | 10/1981 | Cutting . |
| 4,310,103 | 1/1982 | Reilly, Jr. et al. . |
| 4,318,477 | 3/1982 | Kerpe . |
| 4,340,141 | 7/1982 | Fischer . |
| 4,361,408 | 11/1982 | Wirtschafter . |
| 4,382,688 | 5/1983 | Machamer . |
| 4,405,045 | 9/1983 | Villa-Real . |
| 4,412,631 | 11/1983 | Haker . |
| 4,448,541 | 5/1984 | Wirtschafter . |
| 4,473,156 | 9/1984 | Martin . |
| 4,473,884 | 9/1984 | Behl . |
| 4,490,711 | 12/1984 | Johnston . |
| 4,504,153 | 3/1985 | Schollmeyer et al. . |
| 4,526,474 | 7/1985 | Simon . |
| 4,533,346 | 8/1985 | Cosgrove, Jr. et al. . |
| 4,573,606 | 3/1986 | Lewis et al. . |
| 4,588,303 | 5/1986 | Wirtschafter et al. . |
| 4,596,558 | 6/1986 | Smith et al. . |
| 4,616,316 | 10/1986 | Hanpeter et al. . |

(List continued on next page.)

Primary Examiner—John P. Lacyk
Assistant Examiner—Samuel Gilbert
Attorney, Agent, or Firm—Orrick, Herrington & Sutcliffe, LLP

[57] ABSTRACT

A method and system for a health network comprising a facility, operated by a party other than the patient or health care provider, for collecting and routing information pertaining to the health care of a patient to the patient and the health care provider. The health network utilizes two-way communication between the patient and the facility, and the health care provider and the facility. In one embodiment, the facility receives treatment instructions from the health care provider that are specifically developed for each patient. Algorithms are developed based on such instructions. The algorithms are then programmed into an appropriately configured message device in the possession of the patient. The patient is prompted by the message device to measure and enter relevant physiological data, e.g., peak flow, etc., as dictated by the treatment instructions. Based on the measured physiological data and the algorithm, messages are displayed on the message device advising the patient of a specific course of treatment, e.g., to administer medicine, to call the health care provider, to go to the emergency room, etc., or, alternatively, such messages can provide more general information related to the patient's current health status. These results can be transmitted to the facility and the health care provider. The algorithm can be modified, as appropriate, to reflect changes in the treatment plan.

25 Claims, 7 Drawing Sheets

U.S. PATENT DOCUMENTS

| | | |
|---|---|---|
| 4,617,557 | 10/1986 | Gordon . |
| 4,627,225 | 12/1986 | Faller et al. . |
| 4,655,026 | 4/1987 | Wigoda . |
| 4,660,991 | 4/1987 | Simon . |
| 4,662,537 | 5/1987 | Wolf et al. . |
| 4,664,289 | 5/1987 | Shimizu et al. . |
| 4,667,845 | 5/1987 | Frazier et al. . |
| 4,685,271 | 8/1987 | Ringer et al. . |
| 4,693,057 | 9/1987 | Rittinger et al. . |
| 4,693,371 | 9/1987 | Malpass . |
| 4,695,954 | 9/1987 | Rose et al. . |
| 4,717,042 | 1/1988 | McLaughlin . |
| 4,725,997 | 2/1988 | Urquhart et al. . |
| 4,730,846 | 3/1988 | Sheehan et al. . |
| 4,736,849 | 4/1988 | Leonard et al. . |
| 4,747,514 | 5/1988 | Stone . |
| 4,748,600 | 5/1988 | Urquhart . |
| 4,763,810 | 8/1988 | Christiansen . |
| 4,766,542 | 8/1988 | Pilarczyk . |
| 4,779,759 | 10/1988 | Seavey . |
| 4,781,696 | 11/1988 | Moulding, Jr. et al. . |
| 4,785,969 | 11/1988 | McLaughlin . |
| 4,790,118 | 12/1988 | Chilcoate . |
| 4,792,333 | 12/1988 | Kidder . |
| 4,805,811 | 2/1989 | Wetterlin . |
| 4,807,757 | 2/1989 | Rappaport et al. . |
| 4,815,767 | 3/1989 | Lambert . |
| 4,819,352 | 4/1989 | Maunand . |
| 4,834,264 | 5/1989 | Siegal et al. . |
| 4,838,453 | 6/1989 | Luckstead . |
| 4,869,392 | 9/1989 | Moulding . |
| 4,905,866 | 3/1990 | Bartell et al. . |
| 4,915,256 | 4/1990 | Tump . |
| 4,939,705 | 7/1990 | Hamilton et al. . |
| 4,942,544 | 7/1990 | McIntosh et al. ............. 364/413.02 X |
| 4,953,745 | 9/1990 | Rowiett, Jr. . |
| 4,955,371 | 9/1990 | Zamba et al. . |
| 4,971,221 | 11/1990 | Urquhart et al. . |
| 4,975,842 | 12/1990 | Darrow et al. . |
| 4,978,335 | 12/1990 | Arthur, III . |
| 4,998,623 | 3/1991 | Doull . |
| 5,014,851 | 5/1991 | Wick . |
| 5,014,875 | 5/1991 | McLaughlin et al. . |
| 5,016,230 | 5/1991 | Seifers et al. . |
| 5,020,527 | 6/1991 | Dessertine . |
| 5,053,032 | 10/1991 | Barclay et al. . |
| 5,064,071 | 11/1991 | Kerfoot, Jr. . |
| 5,082,113 | 1/1992 | Romick . |
| 5,082,114 | 1/1992 | Bunin . |
| 5,099,463 | 3/1992 | Lloyd et al. . |
| 5,142,484 | 8/1992 | Kaufman et al. ............. 364/413.02 X |
| 5,152,422 | 10/1992 | Springer . |
| 5,154,296 | 10/1992 | Cutler . |
| 5,157,640 | 10/1992 | Backner . |
| 5,163,559 | 11/1992 | Bunin . |
| 5,176,285 | 1/1993 | Shaw . |
| 5,181,189 | 1/1993 | Hafner . |
| 5,215,079 | 6/1993 | Fine et al. . |
| 5,219,095 | 6/1993 | Shimizu et al. . |
| 5,221,024 | 6/1993 | Campbell . |
| 5,251,757 | 10/1993 | Relyea et al. . |
| 5,259,531 | 11/1993 | Bennett . |
| 5,263,596 | 11/1993 | Williams . |
| 5,284,133 | 2/1994 | Burns et al. . |
| 5,286,258 | 2/1994 | Haber et al. . |
| 5,307,263 | 4/1994 | Brown ........................ 364/413.04 X |
| 5,310,060 | 5/1994 | Bitner et al. . |
| 5,339,821 | 8/1994 | Fujimoto ................. 128/903 |
| 5,390,238 | 2/1995 | Kirk et al. ......... 364/413.04 |
| 5,542,420 | 8/1996 | Goldman et al. ........ 128/630 |

METHOD AND APPARATUS FOR A PERSONAL HEALTH NETWORK

This application is a continuation of application Ser. No. 08/518,783 filed on Aug. 24, 1995 which is a continuation in part of Ser. No. 08/334,936, filed Nov. 7, 1994 now abandoned.

FIELD OF THE INVENTION

The invention relates to a system, methods and apparatus for monitoring a person's health, and more particularly to a comprehensive patient management system.

BACKGROUND OF THE INVENTION

Outpatient management of chronic disease may be ideally described as a series of discrete tasks that are interrelated and modulated by information flowing back to the primary health care provider. The elements of outpatient care thus include (1) prescribing a treatment, typically drug-based; (2) a patient independently obtaining the prescribed medication, e.g., filling a prescription at a pharmacy and/or purchasing over-the-counter medication; (3) the patient talking the medication as prescribed; (4) monitoring the effects of the self-medicating treatment; and (5) modifying the treatment based on patient response.

In the traditional model of outpatient management, the information interchange steps (4) and (5), critical to successful treatment programs, occur sporadically. Oftentimes, the exchange occurs during a follow-up visit to the primary care provider or to an emergency room or hospital. Further, the information flow was typically one way, from the physician to the patient.

More recently, in the era of the patient as consumer and health care reform, this situation has changed dramatically. The information flow is no longer so sporadic or one way, but the process of closely monitoring outpatient treatments is inconvenient to both the patients and health care providers. For the patient, it means numerous trips to the doctor's office, often for simple matters like a blood pressure check, that could as easily be performed at home. For the physician, close monitoring is inefficient, both because the issues are routine and it limits the ability to increase the number of patients under management. As a result, the known processes of outpatient management result in many patients "falling through the cracks" and consuming needless and expensive resources for trivial or routine follow-up care.

A wide variety of devices have been proposed to improve outpatient management of the chronically ill. Most such devices are directed to improving patient health through increasing compliance with a medication regimen.

U.S. Pat. No. 4,490,711 discloses a programmable multiple alarm timing device. The device may be programmed for up to a selected number of alarms per day. As the alarm is silenced, a counter is incremented. Thus, the counter indicates how many times the user was alerted to take his or her medication. The counter can be interrogated by pushing a button on the device which will cause the count to appear on an LCD included with the device. A memo book is used in conjunction with the timer.

U.S. Pat. No. 4,504,153 discloses a pharmacist-programmable/physician-programmable medication prompting system wherein a pharmacist/doctor inputs data regarding a medication schedule into the memory of a prompting device which generates a prompting signal according to the schedule. The prompter may be incorporated in the cap of a mechanized medication container. The cap of the container may only be opened when the prompting signal is present. Removal of the cap produces a reset signal terminating the prompt. A counter counts the number of times the reset signal is generated, providing a compliance record.

U.S. Pat. No. 4,695,954 discloses a medical dispenser for dispensing medications to a patient at prescribed times. The device includes apparatus for sensing whether medication is being taken as it becomes available. A nursing home/hospital version has a transmitter and antenna that transmits, in real time, patient compliance information to a nursing station. Also, stored patient compliance information can be printed out. A home version of device does not transmit compliance information, but this information can be retrieved from the display on the device itself.

U.S. Pat. No. 4,975,842 discloses an electronic patient diary that allows a patient to electronically log the onset and end of a preselected health event, such as a pain episode, and subjectively assess some characteristic of the event, i.e., the extent of the pain. All information is recorded in memory and may be downloaded to an external computer. The device can also prompt the user regarding the time and dosage of medication.

U.S. Pat. No. 5,157,640 discloses an electronic watch that may be programmed by direct link to a pharmacist's host computer to store a medication regimen. When a medication is to be taken, an alarm is sounded, and the medication and dosage are identified on the display of the watch. The watch is programmed by placing it in a cradle which is in communication with the host computer.

The prior art falls far short of providing a comprehensive outpatient management system. Most prior art devices are simply directed to the compliance issue.

Thus there is a need for a comprehensive outpatient management system which evaluates compliance with a medication regimen, monitors the effect of the treatment, allows 2-way information exchange between the provider and the patient, and reduces the physician's burden of closely monitoring outpatient treatment.

SUMMARY OF THE INVENTION

The aforementioned need is met by a system, methods and apparatus for a personal health network. In one embodiment, the health network comprises a host computer which is in communication with a computer of a health care provider, and with a data processor that is in the possession of a patient. A message device, also in the possession of the patient, is adapted to send data to, and receive data from, the data processor. The host computer, which is operated by a party other than the patient or health care provider, functions as a central station for collecting, analyzing and routing data. In one embodiment, the host computer receives, from the health care provider, a treatment plan that is developed specifically for each patient. Algorithms are developed based on such a plan. The algorithms are then programmed into an appropriately configured message device. The patient is prompted by the message device to measure and enter relevant physiological data, e.g., peak flow, etc, as dictated by the treatment plan. Based on the measured physiological data and the algorithm, messages are displayed on the message device advising the patient of a specific course of action, e.g., to administer medicine, to call his health care provider, to go to the emergency room, etc. These results can be transmitted to the facility and the health care provider. The algorithm can be modified by the health care provider, as appropriate, to reflect changes in the treatment plan. As a result, the message device incorporates a customized treatment plan that is updatable based on data provided by the patient and health care provider.

BRIEF DESCRIPTION OF THE DRAWINGS

Further features and advantages of the invention will be apparent upon consideration of the foregoing objects and the following detailed description of preferred embodiments of the present invention, taken in conjunction with the accompanying drawings, in which like reference numerals refer to like elements, and in which:

FIG. 4b shows a preferred embodiment of the alternate implementation of the message device of FIG. 4a;

DETAILED DESCRIPTION OF THE INVENTION

Figure 1:
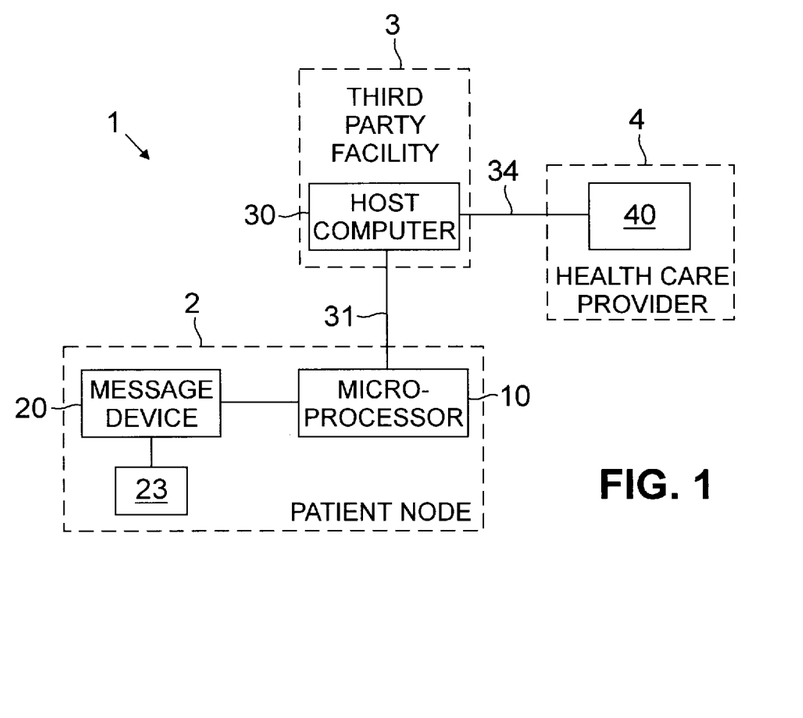
FIG. 1 shows a block schematic diagram of a personal health network in accordance with a preferred embodiment of the present invention.

An embodiment of a personal health network ("PHN") 1 of the present invention is show in FIG. 1. The PHN 1 comprises at least one patient node 2, at least one third party facility 3 and at least one health care provider 4. Each third party facility 3 preferably includes a host computer 30 which is in communication with each patient node 2 being managed by the facility 3 over a communication link 31. The host computer 30 also is in communication with each health care provider 4 for each patient 2, over a communication link 34.

Each patient node 2 includes a data processor 10 and a message device 20. The data processor 10 is in communication with host computer 30 via communication line 31 and is used for downloading information to, and receiving information from, message device 20. The host computer 30 is operated by a third party. The third party is responsible for the operation of the PHN 1 and placement of the software and, in certain cases, hardware, that comprise the various embodiments and/or components of the PHN 1. The host computer 30 of the third party facility 3 functions as a central station for collecting information which can be appropriately routed to the patient 2, health care provider 4 or other location, as discussed in more detail below. The processor 10 and message device 20 are in the possession of a patient 2.

For purposes of clarity only one patient node 2, and third party facility 3, and one health care provider 4 are illustrated in FIG. 1. However, it should be understood that there may be a plurality of patient nodes 2 and a plurality of health care providers 4 in communication with the third party facility 3. Indeed, the third party facility 3 may include more than one such facility (e.g., covering differing geographic or demographic areas), such that patients managed by one facility 3, can be served by health care providers 4 that are in communication with a different facility based on interfacility communications. In this way, the PHN 1 is capable of managing millions of patients 2 and health care providers 4 by appropriate individual identification, addressing and messaging, which communication techniques and protocols are known to those of ordinary skill in the art.

The message device 20 is a portable device, of suitable shape and size to be carried in the pocket, purse or briefcase of a patient. Preferably, the form factor and industrial design of the message device 20 are optimized for acceptance by the intended user, including children and senior citizens. In a preferred embodiment, the message device 20 is powered by a rechargeable power source. The message device 20 receives information from the host computer 30 when the message device is placed in communication with the processor 10. Preferably, the message device 20 and processor 10 have complementary physical structures so that on physical contact, a connection is formed, for example, via male and female connectors, such that information transfer in one or both directions can occur. It is known to those skilled in the art how to implement such devices and their interconnection.

In one embodiment, the message device 20 provides a medication alarm. A patient's entire medication regimen, including dosing intervals, can be downloaded from the host computer 30 to the data processor 1 0 via communication line 31. This information is transferred to the message device 20 when it is in communication with the data processor 10. At the appropriate times, the patient is prompted by audible or tactile alerts. In a preferred embodiment shown in FIG. 2, the message device 20 includes a large-area backlit LCD display 21 so that the name of the medication and dose may be displayed. The patient turns off the alert by activating a switch 22 which also causes a programmable memory 23 to store the date and time the switch was activated. Hence, the message unit 20 stores a record of the so-called compliance data, including the date and time the switch was activated and the medication and dosage that the patient was scheduled to take. In this regard, if the patient's regimen is to take more than one medication at the same time, then each other medication will appear on the LCD display, e.g., one at a time after the switch is activated, e.g., in response to an alarm which occurs for each medication. Alternatively, multiple medications may appear in the LCD display such that activating the switch enters the time and date data for each medication displayed.

When the message device 20 is in communication with the data processor 1 0, the compliance data can be uploaded to the host computer 30. Compliance data can then be evaluated through appropriate software and a report thereof generated and transmitted to one or both of the computer 40 of the appropriate primary health care provider 4 and the processor 10 of patient 2. The report may be electronically transmitted via a suitable communications port 50 over PHN 1, or printed on paper and mailed to the intended recipient. In a further embodiment, the message device 20 may receive other alarm information from the primary health care provider 4. For example, patients can be reminded about a scheduled visit or to schedule a visit.

Figure 3:
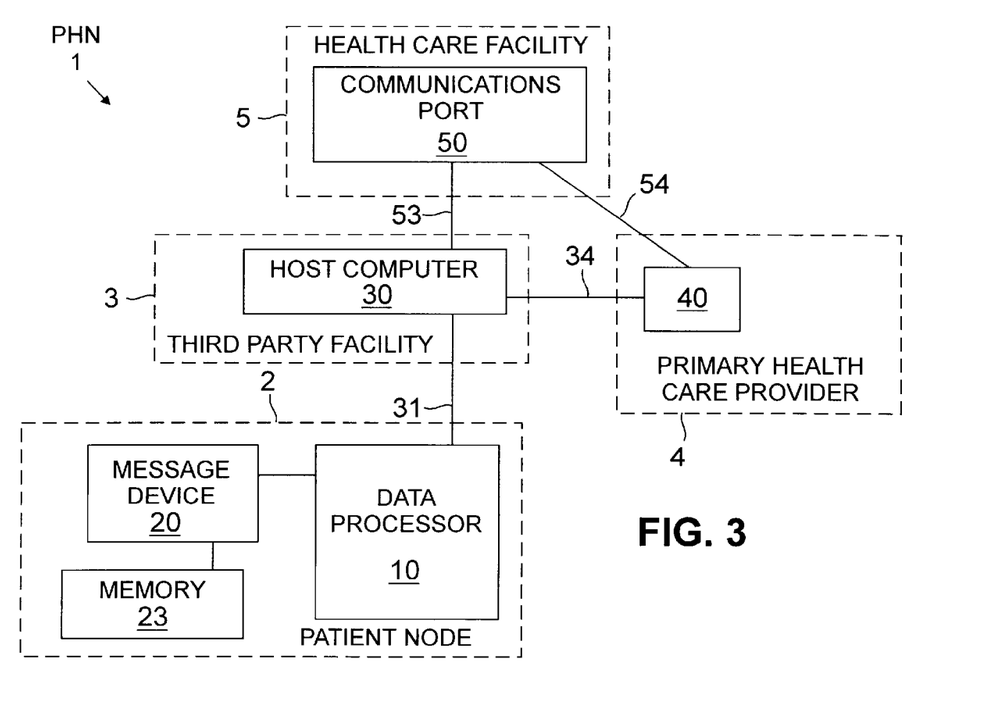
FIG. 3 shows a block schematic diagram of a personal health network in accordance with an alternate embodiment of the present invention.

In a second embodiment of the present invention, shown in FIG. 3, the PHN 1 is also in communication with another health care facility 5 such as a diagnostic laboratory, a pharmacy, a clinic, or a hospital, of which only one is shown for clarity. Thus, in addition to the medication regimen and other information from each primary health care provider 4, the message device 20 may receive information from other health care facilities 5, which is transmitted to host computer 30 via communications line 53 and then downloaded to the data processor 1 0 and the message device 20. Through such a network, patients 2 and doctors 4 can receive the results of tests performed at a lab or hospital 5. Such information from the other health care facilities 5 can also be either directly, via communication line 54, or indirectly, via the host computer 30 through communication lines 53 and 34, communicated to the primary health care provider 4. In addition, statistical reports of the activities of a number of patients can be generated. Such reports are of value to health care management organizations and pharmaceutical manufacturers.

Figure 2:
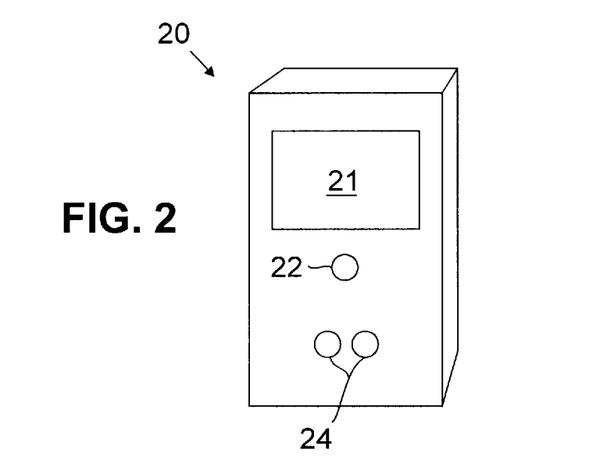
FIG. 2 shows a message device of the network of FIG. 1.

In a further embodiment, the message device 20 can be enhanced to incorporate two-way message capability when coupled to data processor 10. For example, by adding one or more switches 24 (two are shown in FIG. 2), patients can respond to query-type messages, enhancing the ability of providers 4 to track the status of their patients 12. The electronics required to provide the two-way message capability over wire-based coupling and radio frequency based coupling are well known to those skilled in the art. Advantageously, providing the switches 24 on message device 20 ensures that the stored data can be uploaded to the host computer. Alternatively, the switches 24 could be located on processor 10.

In a further embodiment of message device 20, software and adapters can be developed so that personal digital assistants, such as the devices model Wizard available from SHARP Electronics, Inc., device model HP 100LX available from Hewlett Packard, and device model Newton available from Apple Computer, Inc., can communicate with the data processor 10 to receive information from, and deliver information to, the host computer 30 and to generate the alerts for medication regimen, store the patient compliance data, and to provide a display of sales information downloaded from data processor 1 0 and for two-way communication with data processor. Standard data communications can be used and these can be easily created by persons of ordinary skill in the art.

In a further embodiment of data processor 10, a patient-owned computer such as a personal computer (or workstation) or personal digital assistant could be used in place of a dedicated data processor, provided that the host computer 30 is provided access to the personal computer and can establish communications therewith in a similar manner as the data processor 10 described herein.

Figure 4A:
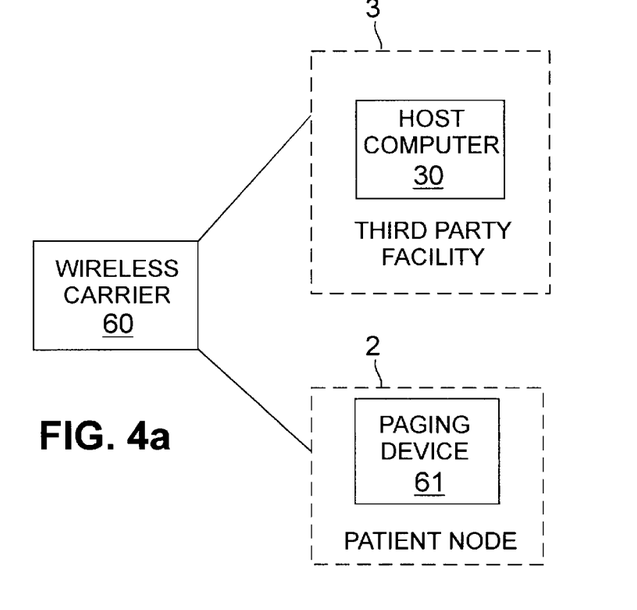
FIG. 4a shows an alternate implementation of the message device and data processor of FIG. 1.

FIG. 4a shows a further embodiment of the PHN 1 wherein the host computer 30 is in communication with a wireless carrier 60 to provide medication reminders and messaging capabilities for patients who own/lease paging devices 61. Wireless carrier 60 thus receives instructions form host computer 30 to deliver particular messages to specific patients 2 at predetermined times. Wireless carrier 60 then "telephones" the patient's pager 61 in a conventional manner, or under control of an automatic operator and delivers the message, activating the pager 61 alarm mechanism. The patient 2 then responds to the pager alarm by pressing the switch. For paging devices 61 having 2-way communication, pressing the switch can provide an acknowledgement of the message delivered, which can be recorded by the wireless carrier 61 as compliance information, which information is then communicated to the host computer 30. Thus, the wireless carrier 60 functions as the data processor 10 and the paging device 61 performs the messaging functions of the message device 20.

Figure 4B:
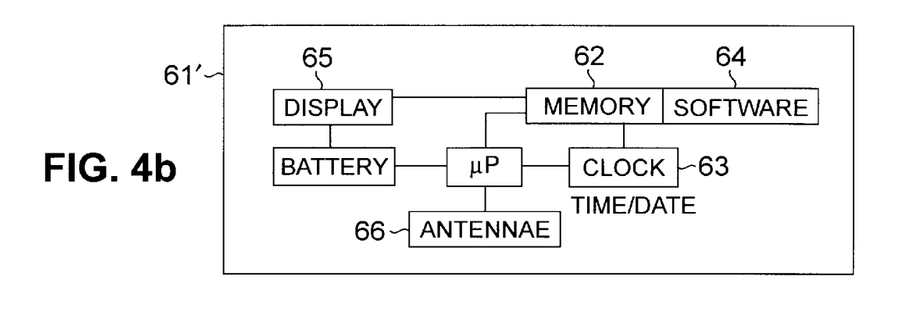

In a preferred embodiment shown in FIG. 4b; a modified paging device 61' is used which includes a non-volatile memory 62, real-time clock 63, antenna 66 and suitable software 64 for storing a medication regimen or other data within the paging device 61 and for causing a message to appear in an alphanumeric display 65 based on the medication regimen or other data in the non-volatile memory 62. In this regard, medication reminders are likely to be repeated daily for a period of time. Instead of having the wireless carrier 60 send the medication alert for each alarm, at an extra cost for sending the same message over and over, the clock 63, software 64 and memory 62 within the paging device 61' can be used to generate the medication alert. This is achieved by sending a message over the wireless carrier 60 that includes the complete dosing regimen, which message is recognized by software 64 and which stores the regimen in memory 62. The software will then actuate the alarm and display the appropriate message as the stored regimen is executed, without prompting by wireless carrier 60. This will reduce communication costs. If the medication regimen is changed, the wireless carrier 60 can re-program the paging device 61' as appropriate. Further, the clock 63 in the paging device 61 is preferably resettable by a general broadcast of a time control signal by the wireless carrier 60. This embodiment is better suited for paging devices having two-way communication capabilities so that safe receipt of the downloaded regimen can be confirmed.

As previously noted, the message device 20 is placed in a communication with the data processor 10 to receive information from, or send information to, the host computer 30. The data processor 1 0 may also incorporate a charger 1 60 for charging the rechargeable power source (not shown) of the message device 20.

Figure 2A:
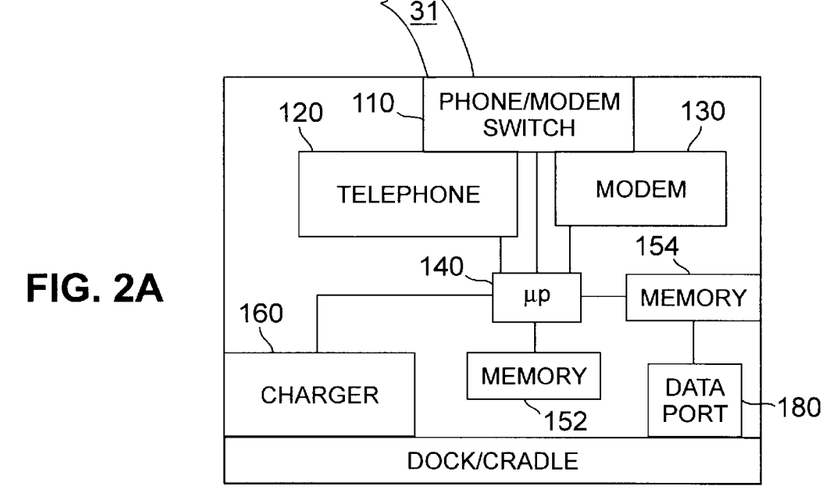
FIG. 2A shows a block schematic diagram of a message device of the network of FIG. 1 in accordance with a preferred embodiment of the invention.

Referring to FIGS. 1 and 2A, one particular embodiment of processor 10 is shown. Processor 1 0 communicates with the host computer 30 by communication link 31 and preferably incorporates a telephone 120 and a modem 130. Information transfer from the host computer 30 to the data processor 10, and the processor 10 to the host computer 30 can occur without patient interaction with the incorporation of suitable electronics and software known to those skilled in the art. In a preferred embodiment, shown in FIG. 2A, one such processor includes a switch 110, a telephone 120, a modem 130, a microprocessor 140, a memory 152 and 154, a charger 160, a dock/cradle 170 and a data port 180. Although not shown, processor 10 may also include a status lamp to indicate whether or not it is properly operating. In a further embodiment, not shown, the data processor 1 0 may include an alphanumeric display and printing capabilities.

The dock/cradle 170 is shaped to receive message device 20 (or a hardware interface unit for a personal digital assistant) so that it couples securely to the charger 160 and data port 180. Once coupled, charger 160 can monitor the power supply of message device 20 and recharge it if necessary. Similarly, the electronics monitor the coupling of the data port 180, and after identifying the message device 20, data transfer can begin. The coupling to charger 160 and data port 180 is preferably a male/female plug interface (not shown) and may be separate components, interfaces or a unique custom interface. In this regard, data sent to device 20 may be stored in memory 154 and data uploaded from device 20 also is stored in memory 154. Memory 152 is shown to represent storage of software instruction for processor 10, but the memory configuration can be adapted based on design preference to have one or multiple memory devices. Switch 110 is used to discriminate incoming voice telephone calls from incoming data telephone calls so that the communication between processor 10 and host computer 30 can occur automatically without patient involvement. Preferably, such communications are scheduled for a time, e.g., at night, when telephone tariffs are least expensive and the user is likely to be at home with message device 20 coupled to processor 11.

Figure 5:
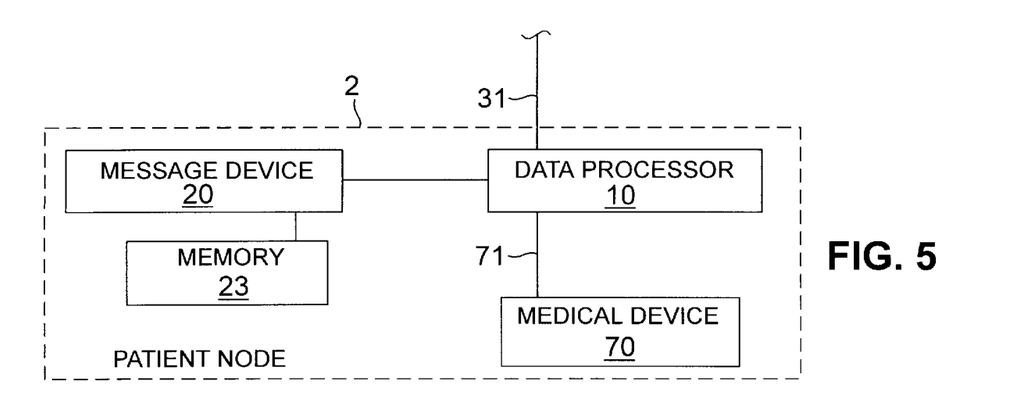
FIG. 5 shows an alternate embodiment of the personal health network of the present invention wherein compatible medical devices communicate with the data processor.

In a preferred embodiment as shown in FIG. 5, the data processor 10 is adapted to accept information input 71 from a medical device 70 that is network compatible. Tracking patient response to medical treatments outside of a health care setting (hospital, hospital, doctor office, clinic) require patients to monitor their blood pressure, blood sugar, pulse rate and other important physiological parameters. A clinician will rarely receive such data, and, even when it is received, it is subject to errors in reporting by the patient. Further, because the data is usually handwritten and previously recorded, it may be difficult to interpret and/or reconstruct accurately.

Accordingly, through the use of a custom interface to translate a signal of the medical device 70 corresponding to the measured parameter into a signal form acceptable to processor 10, the data obtained from basic medical devices 70, such as blood pressure, pulse, blood glucose meters, pulmonary function, cholesterol, etc., can be stored whenever the data is obtained, and then uploaded to the host computer 30 through the data processor 1 0 and/or message device 20. The design of such interfaces and the incorporation of such interfaces into devices 70 are straightforward and within the capabilities of those skilled in the art.

The host computer 30 receives data from the various information sources previously discussed, such as the message device 20, PHN compatible medical devices 70, the primary provider 4, and other health care facilities 5 (e.g., lab, pharmacy, hospital, or a secondary care provider (e.g., a medical specialist such as a surgeon, etc.)). Using appropriate software, the host computer 30 analyzes data received from the various sources noted above, generates a report and forwards it to the primary provider 4, or to some other location 5 as appropriate. In this way, the primary provider 4 can receive periodic reports indicative of the patient's well-being and access the efficacy of the prescribed therapy without consuming the provider's office visit time or the patient's time for a personal visit.

Though appropriate software, the host computer 30 provides a variety of other network-related functions including communications, network management, database manager, error/reliability manager and message/mail manager. The host computer 30 is preferably a main frame computer, although other hardware platforms are acceptable.

In place of the host computer 30, one or more employees/representatives of the third party 3 may collect information, generate and maintain a record of information pertaining to a patient's health and transmit information either directly or indirectly to the patient 2, health care provider 4, or other location via telephone, facsimile transmission, electronic mail, or other communication means.

Figure 6:
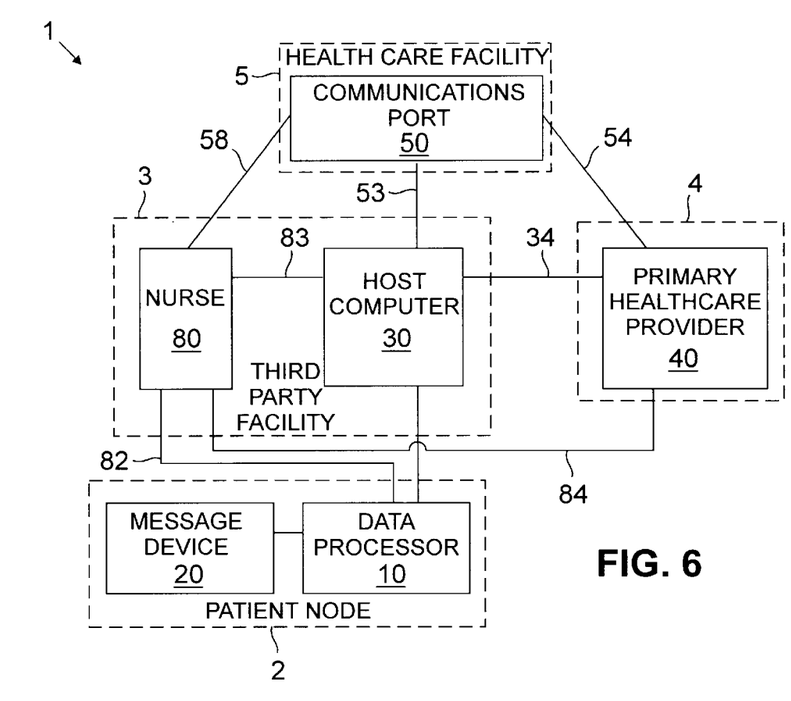
FIG. 6 shows an embodiment of the personal health network of the present invention which includes a case manager nurse.

In an alternate preferred embodiment of the PHN 1 shown in FIG. 6, a case manager nurse 80 may be used to provide additional patient management. The case manager nurse 80 communicates with the patient by communications line 82, which may be a voice telephone, data facsimile or other means. Preferably, the case manager nurse has access to a computer and a modem for receiving information from computers at other health care facilities 5, for example, via communication line 58, and receive information from and provide information to a computer of the primary provider 4 via communication line 84, and host computer 30 via communication line 83. Alternately, the case manager nurse 80 can communicate with health care provider 4 and facility 5 indirectly through host computer 30. The case manager nurse 80 can be an employee of the third party 3 as illustrated in FIG. 6, or of the health care provider 4. Alternatively, the function of the case manager 80 can be handled by an existing nurse-based case management organization, such as Access Health located in Rancho Cordova, Calif.

In some of the above-described embodiments, patient information including physiological data obtained from medical devices 70 is collected over a period of time, e.g., days, and then analyzed and reported to the primary provider 4. The primary provider 4 reviews such data and then may adjust the patient's treatment regimen as appropriate. In certain instances, however, a much quicker response to changes in a patient's condition is necessary. In a further preferred embodiment of the present invention, the PHN 1 can be used to provide a customized patient management program 110 that provides an immediate response to changes in a patient's condition.

In one embodiment of a customized patient management program 110, logic sequences or algorithms 115 are developed based on a treatment plan or guidelines for a specific patient, which plan is provided by the primary provider 4. Such algorithms 115 can be converted to code suitable for implementation in a processor. In a preferred embodiment, the code corresponding to the algorithm can be stored in an appropriately configured message device 20 that can be accessed as required by the patient. The algorithm 115 accepts as input at least one indicia of the patient's then current health status. Such indicia can include a measurement of a physiological parameter such as pulse rate, peak flow, blood pressure and the like. The input is processed according to the algorithm, and the results of the processing are delivered to the patient 2 as a message. The information content of the message can be medical advice, i.e., a directive for the patient to take a specific action, or more general information directly or indirectly related to the health status of the patient at a given time based on the data inputted to the algorithm 115. Since the treatment plan is developed specifically for the patient, and since the algorithm 11 5 based on the treatment plan accepts an indicia of the patient's then current health status, message content is thus customized for the patient and responsive to changes in the patient's health status. An example of such a customized patient management program 110 is described below and in conjunction with FIGS. 10a and 10b.

EXAMPLE 1

A primary provider 4 has two asthma patients, 2a and 2b. The primary provider 4 has transmitted the following exemplary treatment parameters to the third party facility 3 for monitoring under the customized patient management program 110:

| Parameter | Patient 2a | Patient 2b |
| --- | --- | --- |
| Baseline peak flow (BPF) | 650 | 600 |
| Peak flow checks | 9 AM | 7 AM & 5 PM |
| Asthma triggers | Pollen | Cold temperature |
| Prevent medicine | None | Azmacort ™ 2 puffs 9 AM & 6 PM |
| Yellow Zone threshold | ≦80% of BPF | ≦70% of BPF |
| Yellow Zone treatment | Albuterol ™ 3 puffs Wait 30 minutes Repeat peak flow; if ≦80%, then 4 puffs Albuterol ™ and call Primary Provider | Albuterol ™ 4 puffs plan Wait 15 minutes Repeat peak flow and call Primary Provider |
| Red Zone threshold | ≦50% of BPF | ≦60% of BPF |
| Red Zone treatment plan | Albuterol ™ 4 puffs and call Primary Provider | Albuterol ™ 4 puffs and go to emergency room |

Figure 10A:
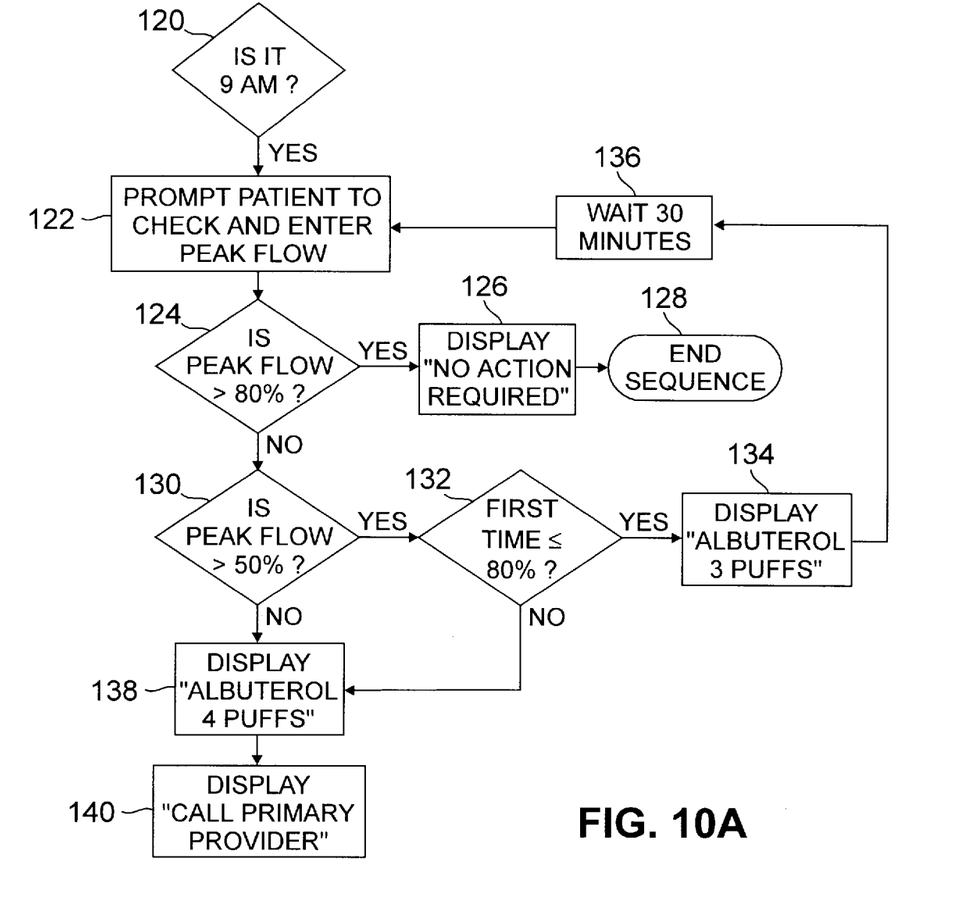
FIG. 10a shows an algorithm based on an exemplary treatment plan for a first asthma patient.
Figure 10B:
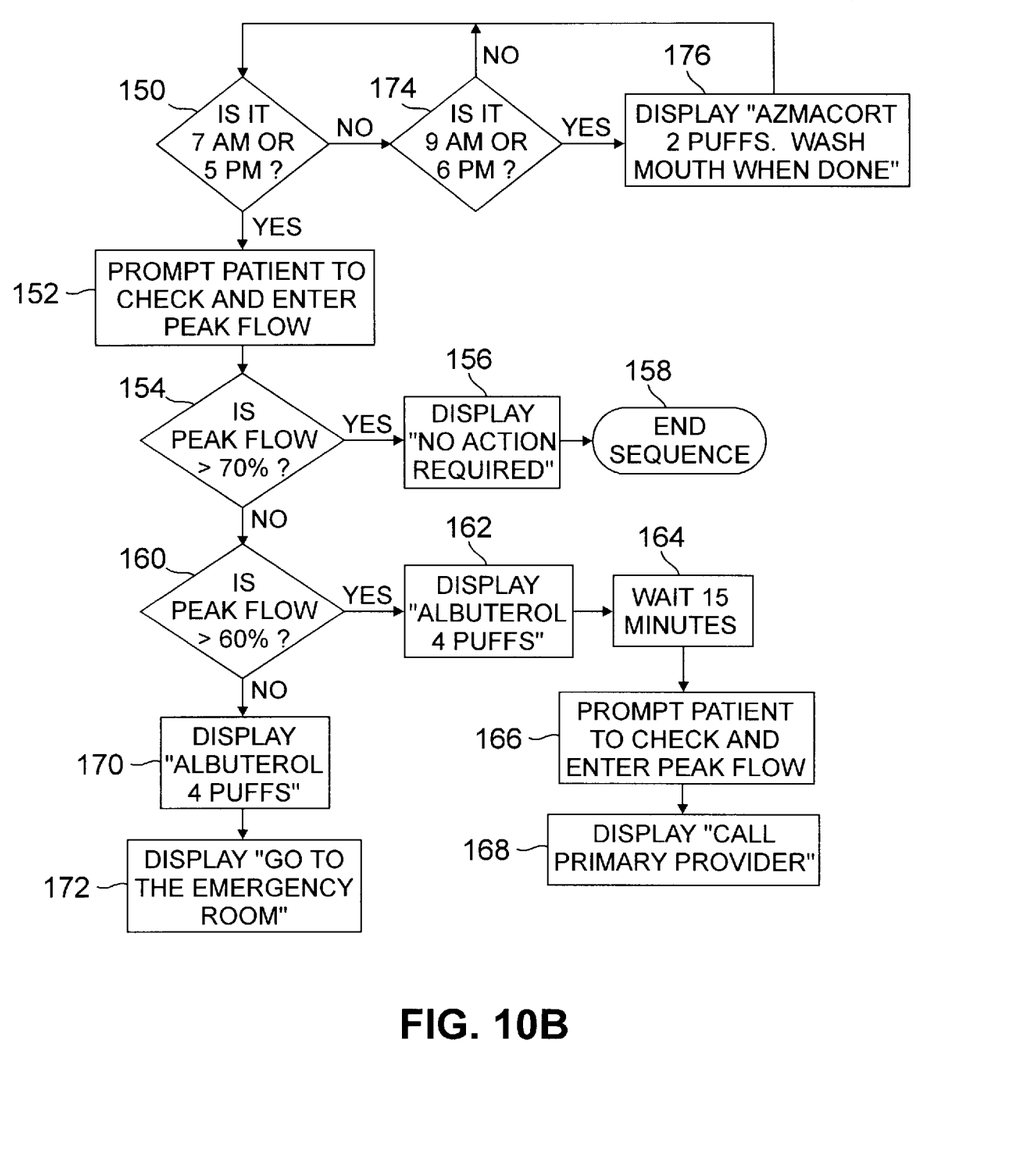
FIG. 10b shows an algorithm based on an exemplary treatment plan for a second asthma patient.

The third party facility 3 develops algorithms 115a and 115b, as illustrated by the exemplary flow charts shown in FIGS. 10a and 10b, based on the treatment parameters. A sequence of steps corresponding to these algorithms 115a, 115b are then programmed into either the host computer 30, the processor 10 or an appropriately configured message device 20, preferably the latter.

Referring to FIG. 10a, patient 2a is prompted in step 122 to measure and enter her peak flow at 9 A.M. In step 124, the logic checks to see if the measured peak flow is greater than eighty percent of patient 2a's baseline peak flow (BPF). If it is, a message will be displayed indicating that no further action is required. If it is not, a second check is performed to see if the measured peak flow is greater than fifty percent of patient 2a's baseline peak flow. If it is not, step 138 causes a message to be displayed on the message device 20 directing the patient to administer 4 puffs of Albuterol™, and step 140 causes a message to be displayed directing the patient to call her primary provider 4. If the measured peak flow is greater than fifty percent of the baseline peak flow, step 132 checks to see if this is the first time (for that day or for some other time period) that the measured peal flow has been less than or equal to eighty percent of the baseline. If not, processing continues with step 138 and then 140, directing the patient to talk 4 puffs of Albuterol™ and call her primary provider 4. If this is the first time that the peak flow was measured at less than or equal to eighty percent of the baseline, step 134 causes a message to be displayed directing the patient to administer 3 puffs of Albuterol™. After 30 minutes, patient 2a is again prompted to measure her peak flow, and the steps of the algorithm are repeated.

A different algorithm is developed for patient 2b based upon the specific treatment plan supplied for this patient by the primary provider 4. The algorithm developed for patient 2b is illustrated in FIG. 10b.

Referring to FIG. 10b, a check is performed in step 150 to see if it is 7 a.m. or 5 p.m. If it is not 7 a.m. or 5 p.m., a check is performed in step 174 to see if it is 9 a.m. or 6 p.m. If it is either 9 a.m. or 6 p.m., step 176 causes a message to be displayed directing patient 2b to administer 2 puffs of Azmacort™. At 7 a.m. or 5 p.m., step 152 causes the patient 2b to be prompted to check and enter her peak flow. A check is performed in step 1 54 to see if the measured peak flow is greater than seventy percent of the baseline peak flow. If it is, step 156 causes a message to be displayed indicating that no further action is required. If it is not, a check is performed in step 160 to see if measured peak flow is greater than sixty percent of baseline. If it is, step 162 causes a message to be displayed directing the patient to administer 4 puffs of Albuterol™. After fifteen minutes, the patient is prompted to again measure her peak flow and further prompted to contact her primary provider 4. If measured peak flow is less than sixty percent of baseline, step 170 causes a message to be displayed directing the patient to administer 4 puffs of Albuterol™ and step 172 prompts the patient to go to the emergency room.

It should be understood that the foregoing example is provided for the purposes of illustration; algorithms based on other treatment parameters for asthma, as well as other health conditions such as congestive heart failure, diabetes, pregnancy care and the like can be developed and implemented according to the present invention. Further, it should be understood that in other embodiments, other indicia of the patient's health status can be used as input to the algorithm.

Thus, the customized patient management program 110 provides a rapid response to changes in a patient's health. The algorithm 115 is preferably programmed into an. appropriately configured message device 20, rather than the host computer 30 or processor 10, so that the message device does not need to be in communication with such devices to access the treatment protocol. In this context, the message device 20 is preferably a personal digital assistant. Use of a personal digital assistant having suitable programming capabilities facilitates portability. Further, with appropriate ancillary equipment, a communication link can be established with the primary provider 4 so that results can be sent to the provider via facsimile or e-mail. In a further preferred embodiment, the message device 20 is configured by means known to those skilled in the art such that the algorithm can be programmed into the message device 20 at the third party facility 3 or remotely via the various communication links previously described in this specification. If the message device 20 is remotely programmable, the primary provider 4 or the third party facility 3 can conveniently modify the treatment algorithm as appropriate. In the case of less sophisticated message device 20, it can be updated or reprogrammed as necessary from time to time during the time it is connected to processor 10.

Data entry, e.g., the peak flow measurements called for in Example 1, may be entered manually by the patient or by using the compatible medical devices 70 previously described. Alternatively, the requirement to enter the peak flow can be omitted in the simpler, less expensive message devices, which instead display the suitable options for the patient to self-medicate. Although a less desirable operation is achieved by this latter technology, it will nonetheless work sufficiently well to be useful.

In a further embodiment, the customized patient management program 110 utilizes data other than the patient's physiological data, e.g., data pertaining to environmental conditions. The host computer 30, processor 10 or message device 20 is appropriately programmed to receive such data and/or deliver messages to the patient. Returning to Example 1, the asthma of patient 2a can be triggered by pollen. Thus, when the pollen count exceeds a certain threshold, which threshold may be unique to a patient 2a, a message warning patient 2a of a high pollen count in her geographic area can be displayed. Patient 2a can then be prompted to administer Albuterol™ prophylactically. Similarly, patient 2b can be alerted to cold weather days.

Compliance with prescribed therapy is the first requirement for reducing health care costs. Currently, providers have no objective way to track medication consumption in a meaningful way, complicating their ability to determine whether the therapy is working. Compliance is especially challenging when patients must take a plurality of medications several times per day. Medication types and dosing schedules are often changed based on the patient's response to treatment. Insuring compliance with the new or revised schedule further complicates medication management. The lack of meaningful data makes it difficult for pharmaceutical manufacturers to know which dispensing schedule, e.g., once, twice or three times a day, is more likely to be successful from both the patient compliance standpoint and the successful therapy standpoint. This information is useful not only for the form and/or architecture of the medication (capsule, caplet, pill, liquid, aerosol, time release microcapsule, etc.) and production planning, but for educating doctors as to how best to prescribe a medication for a patient, in view of the patient's lifestyle and the available dosing regimens. In this regard, the pharmaceutical companies have assumed an important role in educating doctors as to the benefits and cost of medications, but do not always have adequate information to suggest the best program.

Figure 7:
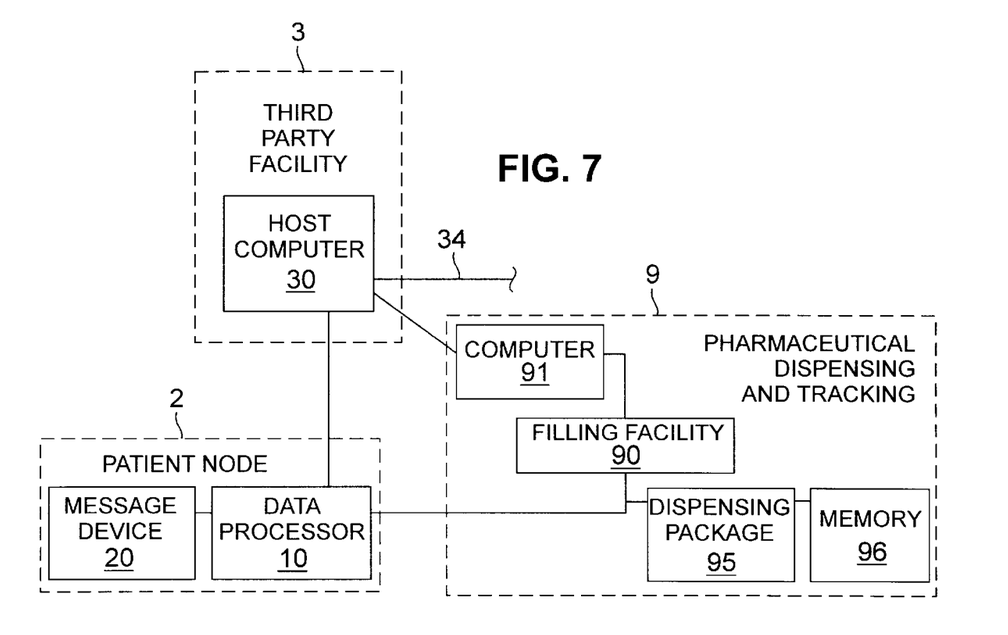
FIG. 7 shows an embodiment of the present invention which incorporates a pharmaceutical dispensing and tracking system.

In another embodiment shown in FIG. 7, a pharmaceutical dispensing and tracking system 4 is included in the PHN 1.

The pharmaceutical dispensing and tracking system 9 comprises a filling facility 90 for filling prescriptions and a dispensing package 95 for storing and dispensing medication. Preferably the filling facility 9 includes a computer 91 for receiving prescription information from the host computer 30 and suitable computer controlled equipment to fill automatically the dispensing package 95. The design and implementation of such equipment are known to those skilled in the art. Of course, the filling facility 90 also can use a prescription directly ordered by the doctor, by telephone, fax or original slip, and the filling could be manually assisted or completely manual. In addition, the dispensing of medication could be by conventional pill bottles such that the patient is responsible for loading the dispensing device 95. Although the alternate systems are less reliable, each will satisfy the requirements of the systems. It is contemplated however, that the prescription information is at some point provided to host computer 30 and to the filling facility 90 for electronic storage in respective databases.

Figure 8:
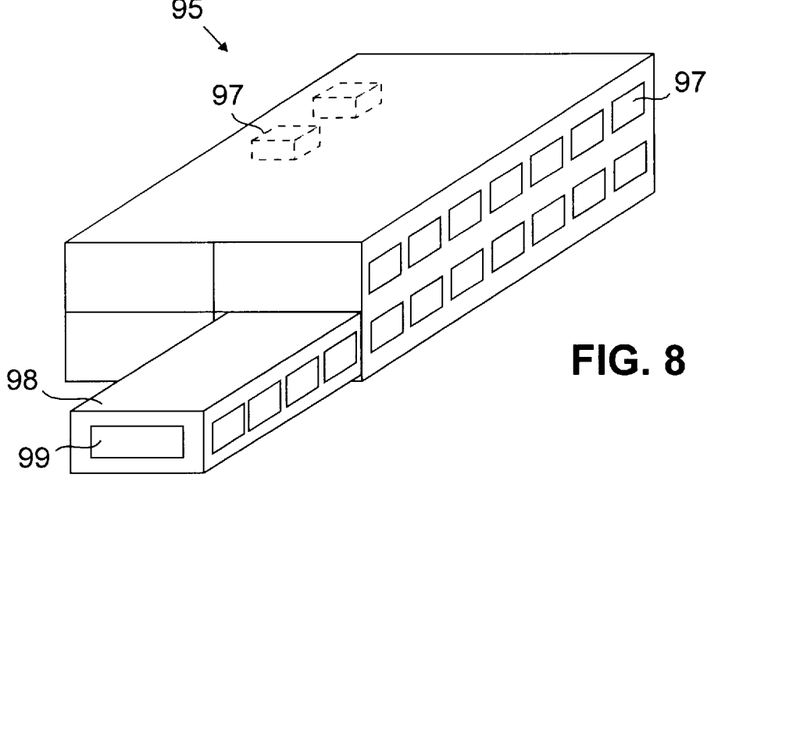
FIG. 8 shows an embodiment of a dispensing package of FIG. 7.

In the preferred embodiment as shown in FIG. 8, the provided dispensing package 95 has a plurality of small compartments collectively numbered 97, each of which has a volume that can hold up to five pills. Preferably there are 28 compartments, corresponding to medication for a week. The dispensing package may contain a multiplicity of different medications distributed among the compartments 97. The dispensing package 95 is sized to fit in a pocket, purse, or briefcase and allows medications to be combined in any order and dispensed in a sequence corresponding to a patient's prescription.

The dispensing package 95 includes a memory 96, which is programmed with a patient's medication regime, at the time of filling. More preferably, package 95 includes all of the aforementioned structure and functions of message device 20. The memory 96 provides a timing/alarm function, which, in conjunction with other suitable electronics, alerts the patient to take his or her medication. The memory 96 also records the time and date the medication was dispensed.

The pharmaceutical dispensing and tracking system 9 in the preferred embodiment operates as follows. The patient's prescription information is transmitted to the filling facility 9. Once the data regarding the medication regime is received by computer 91 at the filling facility 90, the dispensing package 95 is filled automatically with the medication. Information concerning how to use the dispensing package 95, the drugs it contains, and other relevant information is placed in a mailer with the dispensing package 95 and mailed to the patient 2.

In a further embodiment of the pharmaceutical dispensing and tracking system 9, the patient retains possession of dispensing package 95 and receives from the filling facility the cartridges 98, containing the medications, to be loaded into the dispensing package 95. Each cartridge 98 preferably is encoded using a one or two dimensional bar code or a magnetic record, e.g., stripe 99, or other data storage medium such as a memory device or a resistor code, which contains data indicative of the medication contained in the cartridge 98 and optionally the complete medication regimen. This data is interpreted by a reading device associated with the processor 10, located at the patient's home, so that the data processor 10 then programs the dispenser 98 or the dispensing package 95. Alternatively, the reading device could be incorporated in the dispensing package 95.

At each dispensing interval, the patient is alerted. At an alarm, the patient presses a button on the dispenser that permits the release of medication to be taken at that time. As previously noted, pressing the button also stores, in memory 96, the time and date medication was dispensed as a compliance record. Pressing the button also may cause the medication to be released, e.g., into a holding tray.

Figure 9:
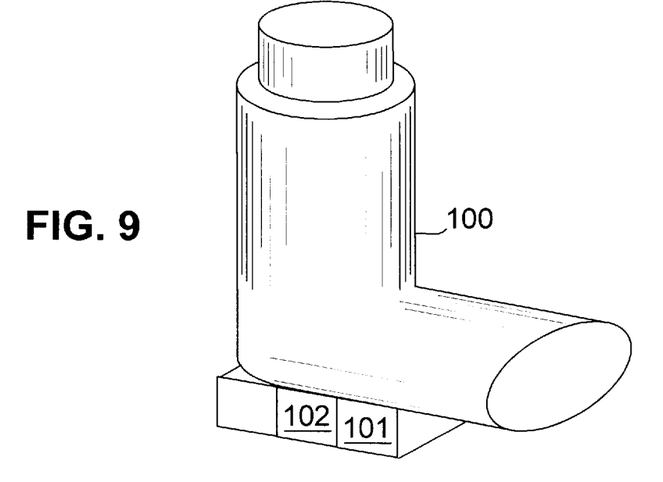
FIG. 9 shows an embodiment of a dose inhaler adapted for use with the system of FIG. 7.

For inhaled medications, an aerosol dose inhaler 100, shown in FIG. 9, may be used. The dose inhaler 100 comprises a memory 101 and suitable electronics for recording the number of times the patient activates the dose inhaler 100. Dosing intervals can be programmed into a device 100 equipped with an alarm function (i.e., when the dose inhaler 100 includes the structure and functions of message device 20) via the processor 10. In addition, in one embodiment, the memory 101 may be a simple counter incremented by actuation of a microswitch which can be interrogated by processor 10 and reset.

In a preferred embodiment, the dose inhaler 100 incorporates suitable flow sensors 102 to monitor and/or track a patient's lung function and dose delivery as are known to persons of ordinary skill in the art.

The memories 96 and 101 can be interrogated when the dispensing package 95 or inhaler 100 is returned to the filling facility 90 by the patient, e.g., by a prepaid return mailer. The memory contains patient identifying information as well as compliance data. Alternatively, the memories can be interrogated by the data processor 10. Thus, the dispensed pharmaceuticals can be readily tracked.

Although it is preferred to use a host computer 30, a data processor 10 and a message device 20 to practice the present invention, other arrangements of elements that provide comparable functions are within the contemplated scope of the present invention. One such arrangement is described in the Example below.

EXAMPLE 2

The elements of this embodiment of a PHN according to the present invention include a wireless paging service, an alphanumeric pager, an electronic blood pressure cuff, a scale, a touch-tone telephone, a toll-free 800 telephone number and appropriate software for accepting and storing information transmitted using the keypad of the touch-tone phone, and a third party 3, e.g., not the patient or health care provider.

The alphanumeric pager, the electronic blood pressure cuff, the scale and touch-tone telephone are all in the possession of a patient 2. A representative of the third party 3 contacts the patient 2 and health care provider 4 and generates a database containing patient information including the patient's medication regime, scheduled office visits, etc. The third party 3 conveys information from the database to the paging service. Based on this information, the paging service "telephones" the patient's pager which delivers messages and/or reminders to the patient, e.g., medication reminders (e.g., 9:00 a.m.—FUROSEMIDE 2 PILLS (40 mg)), reminders to check their weight, blood pressure and pulse, and reminders for scheduled office visits and laboratory tests and telephone contact with the third party.

According to schedule, the patient obtains his or her weight, blood pressure and pulse using the scale and electronic blood pressure cuff. The patient 2 then calls the 800 number and transmits the data via the keypad.

Further, there is scheduled telephone contact between the third party 3 and the patient 2. During the phone call, the patient's health is discussed and the information is preserved in a record. At regular intervals, the third party generates a status report based on the information contained in the records. The status report is transmitted via e-mail, facsimile or mail to the patient's primary provider 4. Based upon the subject's reported clinical status, the primary provider may, for example, alter the patient's treatment regime. These changes are transmitted to the third party, where the patient's database is updated. The change in the regime is then transmitted to the paging service.

Thus, the paging service and the 800 number provide some of the two-way communication functions of the processor 10, the pager provides some of the functions of the message device 20, the scale and electronic blood pressure cuff in conjunction with the 800 number provide some of the functions of the network compatible medical device 70, and the third party 3 provides some of the functions of the host computer 30. This embodiment also includes a case manager nurse 80 who is supplied by the third party.

One skilled in the art will appreciate that the present invention can be practiced by other than the described embodiments, which are presented for purposes of illustration and not of limitation.

I claim:

1. A method for providing a customized out-patent management system comprising:

(a) providing a central station facility with a medical treatment plan specific to a patient, said medical treatment plan comprising a schedule of at least one patient self-directed activity to occur at a corresponding time of action;

(b) determining an occurrence of said time of action within said central station facility;

(c) providing a messaging device associated with said patient wherein said messaging device is equipped with bi-directional communications capability;

(d) providing said messaging device with an event indicator having an active state and an inactive state, the active state corresponding to an indicator of the at least one patient self-directed activity;

(e) transmitting a wireless signal to said messaging device in response to an occurrence of said time of action;

(f) receiving said wireless signal at the messaging device; and (g) placing the event indicator in the active state in response to said received wireless signal to prompt the at least one patient self-directed activity.

2. The method of claim 1 wherein steps (c) and (d) further comprise providing said patient with a paging device having a sound output, and wherein step (g) further comprises generating an audible sound.

3. The method of claim 2 further comprising providing said paging device with a display and wherein step (e) further comprises providing a text message indicating the patient selfdirected activity to be performed, and step (g) further comprises displaying said text message on said display.

4. The method of claim 1 wherein step (d) comprises providing said messaging device with a display, and step (g) comprises displaying a predetermined message in response to said received wireless signal.

5. The method of claim 1 further comprising providing a predetermined message indicating a medication to be taken.

6. The method of claim 1 further comprising providing a predetermined message that is a graphical information for display.

7. The method of claim 1 wherein step (d) comprises providing said messaging device with a tactile sensor, and step (g) comprises actuating said tactile sensor in response to said received wireless signal.

8. The method of claim 1, further comprising performing the patient self-directed activity and obtaining a result thereof, and transmitting from the messaging device for delivery to the central station facility an information corresponding to the obtained result.

9. The method of claim 8 wherein transmitting information further comprises operating a telephone having a touch tone key pad to transmit said information to said central station facility.

10. The method of claim 8 wherein transmitting information further comprises transmitting a wireless signal containing said information.

11. A method for providing a customized out-patent management system comprising:

(a) providing a central station facility with a medical treatment plan specific to a patient, said medical treatment plan comprising a schedule of at least one patient self-directed activity to occur at a corresponding time of action;

(b) determining an occurrence of said time of action within said central station facility;

(c) providing a messaging device associated with said patient wherein said messaging device is a paging device having a sound output with a bi-directional communication capability;

(d) providing said messaging device with an event indicator having an active state and an inactive state, the active state corresponding to an indicator of the at least one patient self-directed activity;

(e) transmitting a wireless signal to said messaging device in response to an occurrence of said time of action;

(f) receiving said wireless signal at the messaging device;

(g) placing the event indicator in the active state in response to said received wireless which generates an audible sound signal to prompt the at least one patient self-directed activity; and (g) transmitting, in response to receipt of the wireless signal, an acknowledgment signal from said paging device, and recording at the central station facility a response acknowledged signal in response to said acknowledgement signal.

12. A method for providing a customized out-patent management system comprising:

(a) providing a central station facility with a medical treatment plan specific to a patient, said medical treatment plan comprising a schedule of at least one patient self-directed activity to occur at a corresponding time of action;

(b) determining an occurrence of said time of action within said central station facility;

(c) providing a messaging device with a bi-directional communication ability;

(d) providing said messaging device with an event indicator having an active state and an inactive state the active state corresponding to an indicator of the at least one patient self-directed activity wherein said messaging device is further provided with a display;

(e) transmitting a wireless signal to said messaging device in response to an occurrence of said time of action;

(f) receiving said wireless signal at the messaging device;

(g) placing the event indicator in the active state in response to said received wireless signal by displaying a predetermined message in response to said received wireless signal to prompt the at least one patient self-directed activity; and (h) transmitting, in response to receipt of the wireless signal, an acknowledgment signal from said messaging device, and recording at the control station facility a response acknowledgment signal in response to said acknowledgement signal.

13. A method for providing a customized out-patent management system comprising:

(a) providing a central station facility with a medical treatment plan specific to a patient, said medical treatment plan comprising a schedule of at least one patient self-directed activity to occur at a corresponding time of action;

(b) determining an occurrence of said time of action within said central station facility;

(c) providing a messaging device associated with said patient;

(d) providing said messaging device with an event indicator having an active state and an inactive state, the active state corresponding to an indicator of the at least one patient self-directed activity;

(e) transmitting a wireless signal to said messaging device in response to an occurrence of said time of action;

(f) receiving said wireless signal at the messaging device;

(g) placing the event indicator in the active state in response to said received wireless signal to prompt the at least one patient self-directed activity;

(h) performing the patient self-directed activity and obtaining a result thereof;

(i) transmitting from the messaging device for the delivery to the central station facility an information corresponding to the obtained result;

(j) providing a case management nurse;

(k) having the case management nurse contact the patient at a predetermined time; and (l) monitoring thereby the patient's self-directed activities.

14. A method for providing a customized out-patent management system comprising:

(a) providing a central station facility with a medical treatment plan specific to a patient, said medical treatment plan comprising a schedule of at least one patient self-directed activity to occur at a corresponding time of action;

(b) determining an occurrence of said time of action within said central station facility;

(c) providing a messaging device associated with said patient;

(d) providing said messaging device with an event indicator having an active state and an inactive state, the active state corresponding to an indicator of the at least one patient self-directed activity;

(e) transmitting a wireless signal to said messaging device in response to an occurrence of said time of action;

(f) receiving said wireless signal at the messaging device;

(g) placing the event indicator in the active state in response to said received wireless signal to prompt the at least one patient self-directed activity;

(h) providing a case management nurse;

(i) having the case management nurse contact the patient at a pre-determined time; and (j) monitoring the patient's self-directed activities in response to step (i).

15. A system of customized out-patient management comprising:

a wireless carrier having a wireless signal output, each wireless output signal having a patient specific code;

a programmable patient specific medical treatment plan comprising at least one patient self-directed activity to occur at a corresponding time of action;

a central station facility containing said patent specific medical treatment plan, the central station being operatively connected to said wireless carrier to issue a patient specific wireless output signal in response to an occurrence of said time of action; and at least one messaging device capable of bi-directional communication associated with said specific patient having a prompt output and an identification code, said messaging device being responsive to said patient specific wireless signal output code corresponding to said identification code to prompt said patient to perform said at least one patient self-directed activity.

16. The system of claim 15 wherein the messaging device prompt output further comprises a visual prompt.

17. The system of claim 16 wherein said visual prompt further comprises a graphic message.

18. The system of claim 16 wherein said visual prompt further comprises an alphanumeric message.

19. The system of claim 16 wherein said messaging device further comprises a paging device.

20. The system of claim 15 further comprising a telephone having touch tone key pad to input data, wherein said central station facility further comprises an input and means for recording data input by a telephone touch tone keypad, said data corresponding to a result of said patient self-directed activity.

21. A system of customized out-patient management comprising:
- a wireless carrier having a wireless signal output, each wireless output signal having a patient specific code;
- a programmable patient specific medical treatment plan comprising at least one patient self-directed activity to occur at a corresponding time of action;
- a central station facility containing said patent specific medical treatment plan, the central station being operatively connected to said wireless carrier to issue a patient specific wireless output signal in response to an occurrence of said time of action; and
- at least one messaging device associated with said specific patient having a visual prompt output and an identification code, said messaging device being responsive to said patient specific wireless signal output code corresponding to said identification code to prompt said patient to perform said at least one patient self-directed activity said messaging device further comprising a paging device wherein said paging device further comprises a bi-directional messaging capability with said wireless carrier, an actuable switch, and a wireless message received output signal, wherein the wireless carrier further comprises means for receiving a wireless message received output signal from said messaging device and means for transmitting a receipt acknowledged signal to said central station facility; and wherein the central station facility further comprises means for recording a response acknowledged signal in response to said receipt acknowledged signal and associating said response acknowledged signal with said wireless signal output.

22. A system of customized out-patient management comprising:
- a wireless carrier having a wireless signal output each wireless output signal having a patient specific code;
- a programmable patient specific medical treatment plan comprising at least one patient self-directed activity to occur at a corresponding time of action,
- a central station facility containing said patent specific medical treatment plan, the central station being operatively connected to said wireless carrier to issue a patient specific wireless output signal in response to an occurrence of said time of action; and
- at least one messaging device associated with said specific patient having a prompt output and an identification code, said messaging device being responsive to said patient specific wireless signal output code corresponding to said identification code to prompt said patient to perform said at least one patient self-directed activity wherein said messaging device further comprises a bi-directional messaging capability with said wireless carrier, an actuable switch, and a wireless message received output signal, wherein the wireless carrier further comprises means for receiving a wireless message received output signal from said messaging device and means for transmitting a receipt acknowledged signal to said central station facility; and wherein the central station facility further comprises means for recording a response acknowledged signal in response to said receipt acknowledged signal and associating said response acknowledged signal with said wireless signal output.

23. The system of claim 22 wherein said wireless received output signal further comprises an obtained result responsive to said at least one patient self-directed activity.

24. A system of customized out-patient management comprising:
- a wireless carrier having a wireless signal output, each wireless output signal having a patient specific code;
- a programmable patient specific medical treatment plan comprising at least one patient self-directed activity to occur at a corresponding time of action;
- a central station facility containing said patent specific medical treatment plan, the central station being operatively connected to said wireless carrier to issue a patient specific wireless output signal in response to an occurrence of said time of action; and
- at least one messaging device associated with said specific patient having a tactile prompt output and an identification code, said messaging device being responsive to said patient specific wireless signal output code corresponding to said identification code to prompt said patient to perform said at least one patient self-directed activity, said messaging device further comprising a paging device wherein said paging device further comprises a bi-directional messaging capability with said wireless carrier, an actuable switch, and a wireless message received output signal, wherein the wireless carrier further comprises means for receiving a wireless message received output signal from said messaging device and means for transmitting a receipt acknowledged signal to said central station facility; and wherein the central station facility further comprises means for recording a response acknowledged signal in response to said receipt acknowledged signal and associating said response acknowledged signal with said wireless signal output.

25. A system of customized out-patient management comprising:
- a wireless carrier having a wireless signal output, each wireless output signal having a patient specific code;
- a programmable patient specific medical treatment plan comprising at least one patient self-directed activity to occur at a corresponding time of action;
- a central station facility containing said patent specific medical treatment plan, the central station being operatively connected to said wireless carrier to issue a patient specific wireless output signal in response to an occurrence of said time of action; and
- at least one messaging device associated with said specific patient having an audible prompt output and an identification code, said messaging device being responsive to said patient specific wireless signal output code corresponding to said identification code to prompt said patient to perform said at least one patient self-directed activity, said messaging device further comprising a paging device wherein said paging device further comprises a bidirectional messaging capability with said wireless carrier, an actuable switch, and a wireless message received output signal, wherein the wireless carrier further comprises means for receiving a wireless message received output signal from said messaging device and means for transmitting a receipt acknowledged signal to said central station facility; and wherein the central station facility further comprises means for recording a response acknowledged signal in response to said receipt acknowledged signal and associating said response acknowledged signal with said wireless signal output.

* * * * *

UNITED STATES PATENT AND TRADEMARK OFFICE
CERTIFICATE OF CORRECTION

PATENT NO. : 5,827,180
DATED : October 27, 1998
INVENTOR(S) : David E. Goodman

Page 1 of 2

It is certified that error appears in the above-identified patent and that said Letters Patent is hereby corrected as shown below:

Column 1, line 23, after "patient" delete "talking," and insert therefor --taking--;
Column 2, line 14, after "version of" insert --the--;
Column 2, line 60, after "flow" delete "etc," and insert --etc.,--;
Column 3, line 51, after "is" delete "show" and insert --shown--;
Column 4, line 42, after "processor" delete "1 0" and insert --10--;
Column 4, line 64, after "processor" delete "1 0" and insert --10--;
Column 5, line 18, after "processor" delete "1 0" and insert --10--;
Column 5, line 53, after "processor" delete "1 0" and insert --10--;
Column 6, lines 1-2, after "instructions" delete "form" and insert --from--;
Column 6, line 36, after "can" delete "re-program" and insert --reprogram--;
Column 6, line 46, after "processor" delete "1 0" and insert --10--; and after "charger" delete "1" and insert --1-- with "60" on line 47;
Column 6, line 50, after "Processor" delete "1 0" and insert --10--;
Column 6, line 63, after "processor" delete "1 0" and insert --10--;
Column 7, line 26, after "(hospital," delete "hospital"; and after "clinic)" delete "require" and insert --requires--;
Column 7, line 41, after "processor " delete "1 0" and insert --10--;
Column 8, lines 57-58, after "algo-rithm" delete "11 5" and insert --115--;
Column 9, line 43, after "measured" delete "peal" and insert --peak--;
Column 9, line 45, after "patient to" delete "talk" and insert --take--;
Column 9, line 64, after "step" delete "1 54" and insert --154--;
Column 11, line 33, after "but" insert --also--;
Column 11, line 58, after "contemplated" insert --,--;

UNITED STATES PATENT AND TRADEMARK OFFICE
CERTIFICATE OF CORRECTION

PATENT NO. : 5,827,180

DATED : October 27, 1998

INVENTOR(S) : David E. Goodman

It is certified that error appears in the above-identified patent and that said Letters Patent is hereby corrected as shown below:

Column 14, line 24, after "patient" delete "selfdirected" and insert --self-directed--;
Column 15, line 26, after "inactive state" insert --,--;
Column 16, line 32, after "at a" delete "pre-determined" and insert --predetermined--;
Column 16, line 35, after "customized" delete "out-patient" and insert --outpatient--;
Column 16, line 43, after "said" delete "patent" and insert --patient--;
Column 17, line 8, after "said" delete "patent" and insert --patient--;
Column 17, line 41, after "said" delete "patent" and insert --patient--;
Column 18, line 8, after "said" delete "patent" and insert --patient--;
Title Page, after "David" delete "F." and insert --E.--;

Signed and Sealed this

Seventh Day of December, 1999

Attest:

*Attesting Officer*

Q. TODD DICKINSON

*Acting Commissioner of Patents and Trademarks*